United States Patent [19]
Chan

[11] Patent Number: 5,741,259
[45] Date of Patent: Apr. 21, 1998

[54] SURGICAL FASTENER DEVICE FOR USE IN BONE FRACTURE FIXATION

[76] Inventor: Kwan-Ho Chan, 4803 1st Pl., Lubbock, Tex. 79416

[21] Appl. No.: 604,868

[22] Filed: Feb. 22, 1996

[51] Int. Cl.$^6$ ................................................ A61B 17/58
[52] U.S. Cl. .......................... 606/74; 606/69; 606/70; 606/71; 606/103
[58] Field of Search .......................... 606/61, 69–71, 606/73–74, 103

[56] References Cited

U.S. PATENT DOCUMENTS

| | | | |
|---|---|---|---|
| 2,501,978 | 3/1950 | Wichman | 606/74 |
| 4,651,724 | 3/1987 | Berentey et al. | 606/70 |
| 5,190,545 | 3/1993 | Corsi et al. | 606/74 |
| 5,324,291 | 6/1994 | Ries et al. | 606/74 |

OTHER PUBLICATIONS

Biomet Medical Products, "BMP Cable System" —1995.
Howmedica, "The Dall–Miles Trochanter Cable Grip System" —1983.
Howmedica, "Dall–Miles Cable Grip System—Mini Cleat" —1995.
Howmedica, "Dall–Miles Cable Grip System—A Versatile Resource to Address the Unpredictable in Revision Hip Surgery" —1995.
Howmedica, "Dall–Miles Cable Grip System—Stainless Steel System" —1993.
Synthes, "Wire Mount" —1996.
Cable-Ready, "Cable-Ready Cable Grip System" —1994.

*Primary Examiner*—Michael Buiz
*Assistant Examiner*—Daphna Shai
*Attorney, Agent, or Firm*—Pandiscio & Pandiscio

[57] ABSTRACT

A surgical fastener for use in bone fracture fixation comprises a top block portion having a bore extending therethrough and adapted to receive surgical cable, and a protrusion extending from an underside of the top block portion and centrally of the top block portion, and adapted for insertion into a compression plate recess which prevents sliding of the fastener along the bone during tightening of the cable around the bone fracture area.

14 Claims, 4 Drawing Sheets

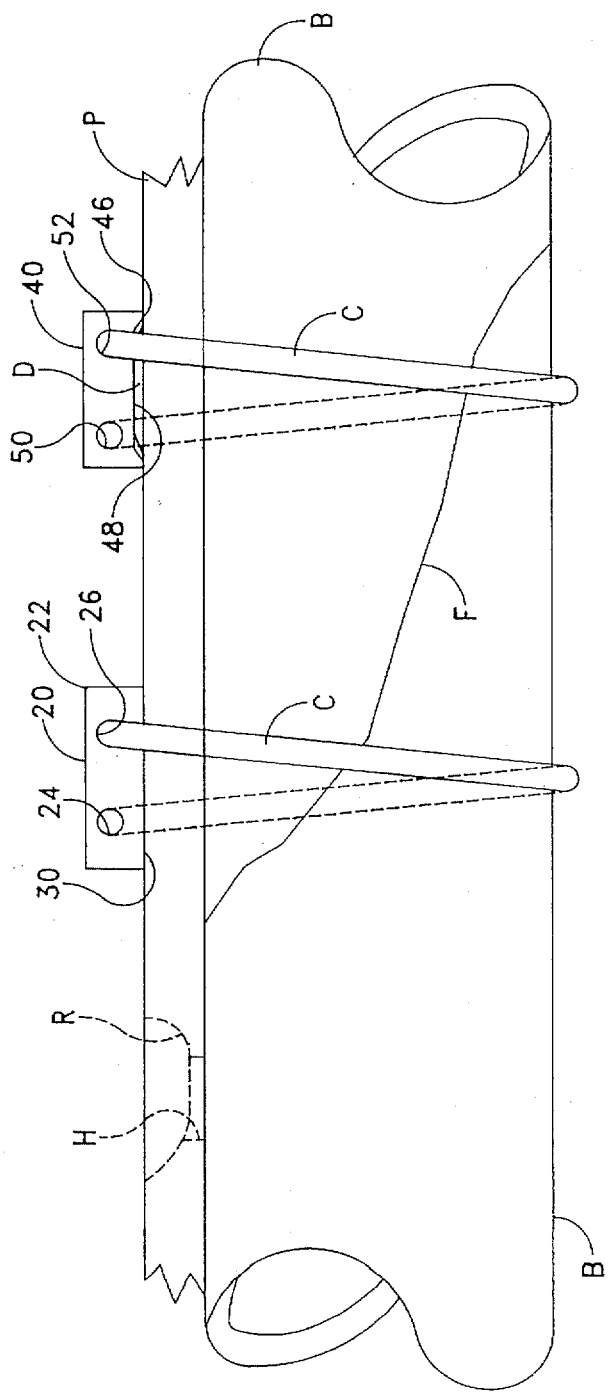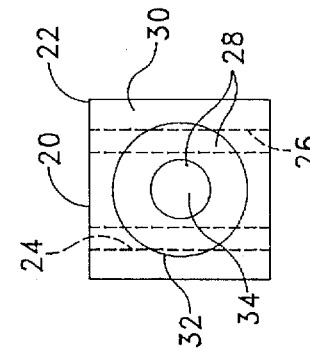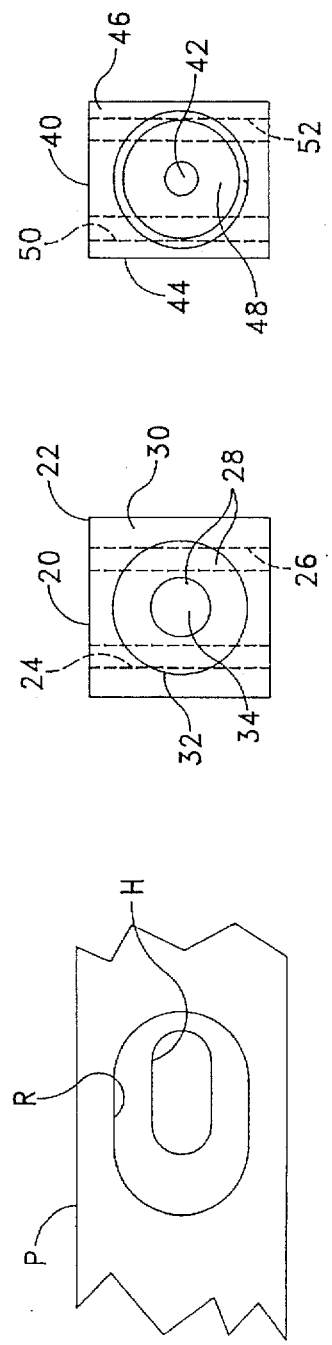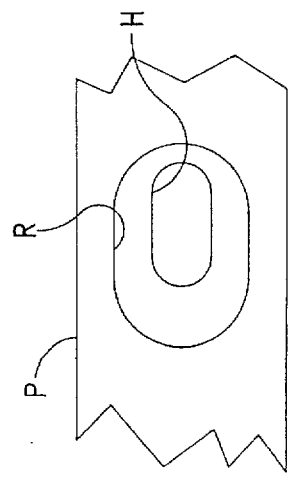

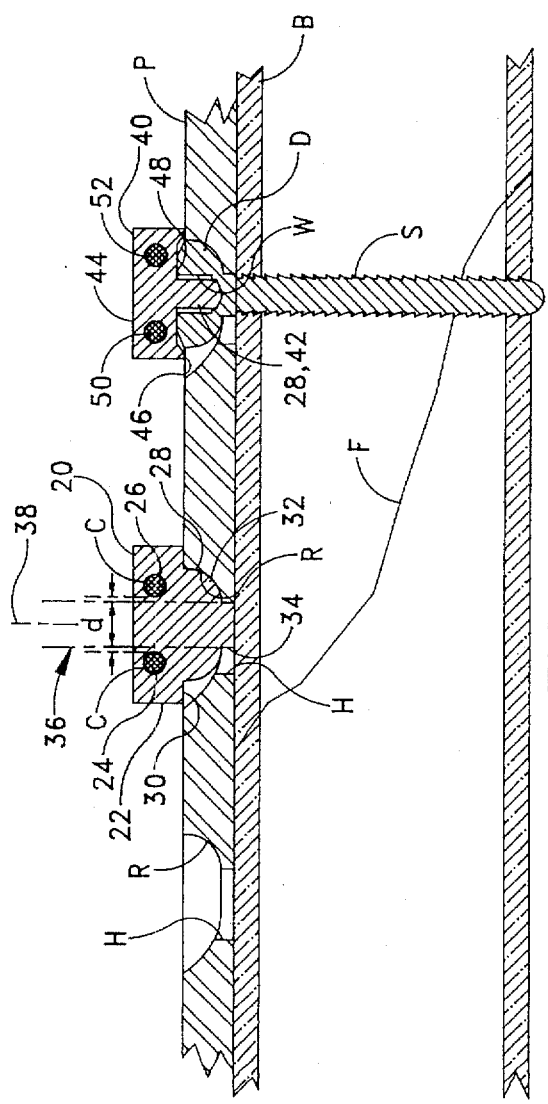
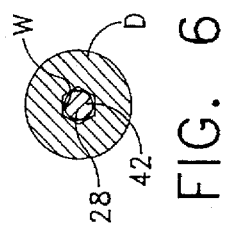
FIG. 6
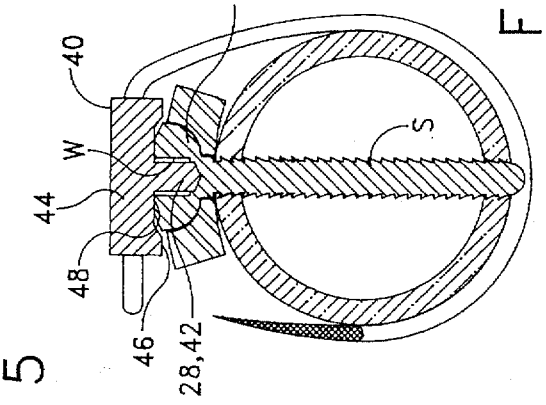
FIG. 8
FIG. 5
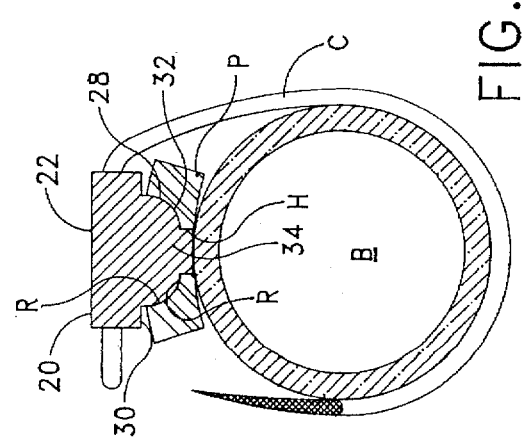
FIG. 7

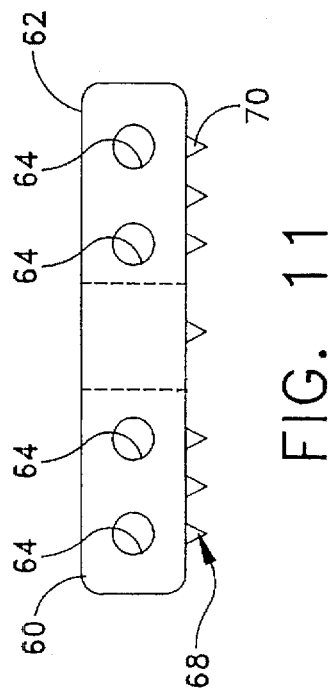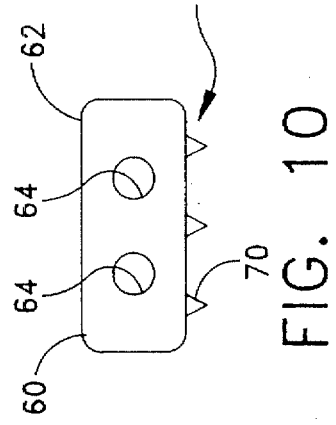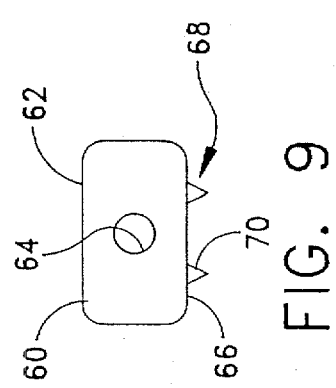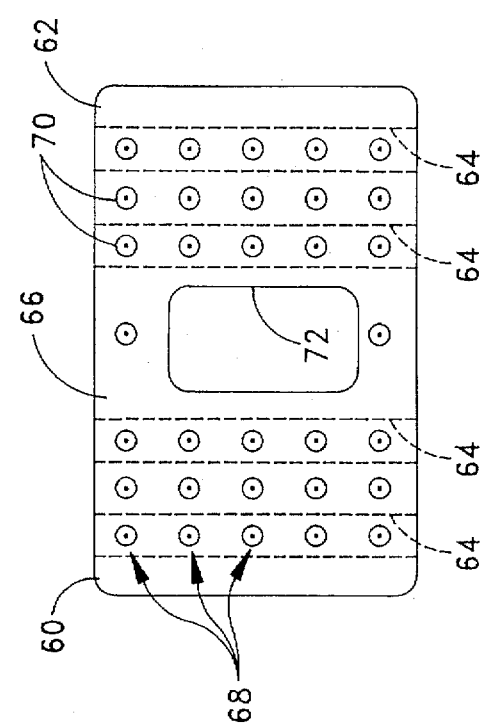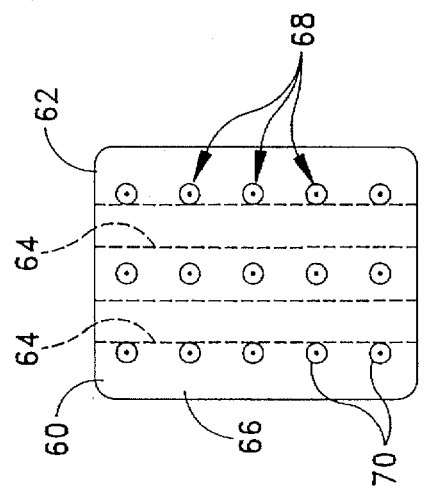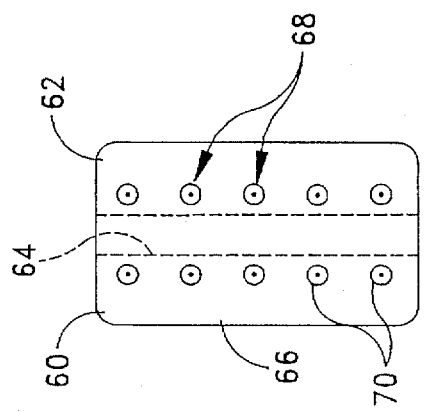

SURGICAL FASTENER DEVICE FOR USE IN BONE FRACTURE FIXATION

FIELD OF THE INVENTION

This invention relates to surgical apparatus and procedures in general, and more particularly to fastening devices, such as crimp devices, for use with surgical cables in fixation of bones during surgeries for fractured bone or bone reconstruction.

BACKGROUND OF THE INVENTION

Bone fracture fixation is an established art. Fixation screws and metal compression plates used in combination for fracture fixation are standard industry wide. The standards are based on designs developed by the Association for the Study of the Problem of Internal Fixation. Therefore, screws and plates made by one manufacturer are geometrically compatible with screws and plates of other manufacturers.

Surgical cables and metal compression plates, used in combination, and without fixation screws, are also well known in the art of fracture fixation. Cables and plates are generally used where the use of screws and plates is not suitable. By way of example, cables and plates are frequently used in fixation of long oblique fractures where the medullary canal has a metal prosthesis in place from prior surgery, such as a hip replacement. The bone cement and metal prosthesis within the bony canal preclude the use of screws for fixation in certain segments of the bone. Fixation with cables or wires is required in such cases. In bones that are osteoporotic, where screw fixation is not practical, fixation with cables or wires is required. Such cables are further used in conjunction with screws and plates, as for example, when the screw strips its threads in deployment, or the screw alone is otherwise deemed insufficient for the fixation at hand. In some instances, it would be helpful to omit the metal compression plate altogether and secure a fracture with only cables, with no screw and no plate.

The cables are used to encircle the bone, or bone and plate, to provide for fixation. In fixation by cable, it is customary to use a fastening device, typically a crimp device which is adapted to be deformed upon the cable for securing the cable in place, encircling the bone in the fracture area. In other fastening devices of this type, the cable is fixed in the fastening device by a holding screw, or by welding, or the like. In general, fixation with cable on the shaft of long bone does not present a problem with migration because the bone in this area is tubular in geometry. However, at the ends of long bone (known as the metaphysis), where there is a significant flare in the geometry, tightening the encircling cable or wire causes the cable and fastening device to migrate towards the narrower section of the bone. Such migration can displace the cable and fastening device from its intended location sufficiently to weaken, or render ineffective, encirclement of the fracture.

To prevent migration of fasteners, some compression plates are provided with slots for receiving and retaining the fastener devices. However, the provision of such a slot renders the location of a screw hole in the same area impractical, and a surgeon is unable to apply a fixation screw in the area of a fastener slot and unable to use a fastener in the area of a screw hole.

Thus, there is a need for an improved fastener adapted for use with known metal compression plates for fixation of bone fractures, and a need for such a fastener as may be used in conjunction with conventional screws and plates in combination. There further exists a need for a fastener device which may be used in conjunction with a compression plate screw hole. There still further exists a need for a fastener for use in fixation of metaphyseal bone without the use of a metal plate. There still further exists a need for such fasteners as will not slide along a compression plate or bone during tightening of the cable during cable deployment.

OBJECTS OF THE INVENTION

Accordingly, one object of the present invention is to provide an improved fastener device for cables in surgical fracture fixation.

Another object of the present invention is to provide an improved cable fastener device which is adapted for use with known metal compression plates for bone fracture fixation, and which does not slide along the plate during tightening of the cable.

Another object of the present invention is to provide an improved fastener device adapted for use with known metal plates and further adapted for use with standard bone fixation screws.

Still another object of the present invention is to provide such a fastener device as may be used in conjunction with a compression plate having screw holes therein.

Still another object of the present invention is to provide an improved fastener device adapted for use in fixation of metaphyseal bone, without the use of a metal plate, which fastener device prevents the cable and the fastener from sliding during tightening of the cable around the bone.

SUMMARY OF THE INVENTION

These and other objects of the present invention are addressed by the provision and use of a novel surgical fastener device for use in bone fracture fixation, the fastener comprising a top block portion having first and second bores extending therethrough and adapted to receive surgical cable, and a protrusion extending from an underside of the top block portion and centrally of the top block portion, and adapted for insertion into a compression plate screw hole recess.

The objects of the present invention are further addressed by the provision and use of a novel surgical fastener device for use in bone fracture fixation, the fastener comprising a block having a plurality of bores extending therethrough and adapted to receive surgical cable, the block having an under-surface with gripper means thereon for engagement with a bone surface.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 1 is a side elevational view of a fractured bone, a compression plate, surgical cables, and first and second embodiments of fastener devices in accordance with the present invention;

FIG. 2 is a top plan view of a portion of the compression plate of FIG. 1;

FIG. 3 is a bottom plan view of the first embodiment of fastener device shown in FIG. 1;

FIG. 4 is a bottom plan view of the second embodiment of fastener device shown in FIG. 1;

FIG. 5 is similar to FIG. 1, but shows the bone, compression plate and fastener devices in section;

FIG. 6 is a widthwise sectional view of a portion of the second embodiment of fastener device disposed in a portion of a fixation screw;

FIG. 7 is a sectional view normal to the section of FIG. 5, illustrating use of the first embodiment of fastener device;

FIG. 8 is a sectional view normal to the section of FIG. 5, and similar to FIG. 7, illustrating use of the second embodiment of fastener device;

FIGS. 9–11 are side elevational views of variations of a third embodiment of fastener device;

FIGS. 12–14 are bottom plan views of the respective fastener devices shown in FIGS. 9–11;

DETAILED DESCRIPTION OF THE PREFERRED EMBODIMENTS

Figure 16:
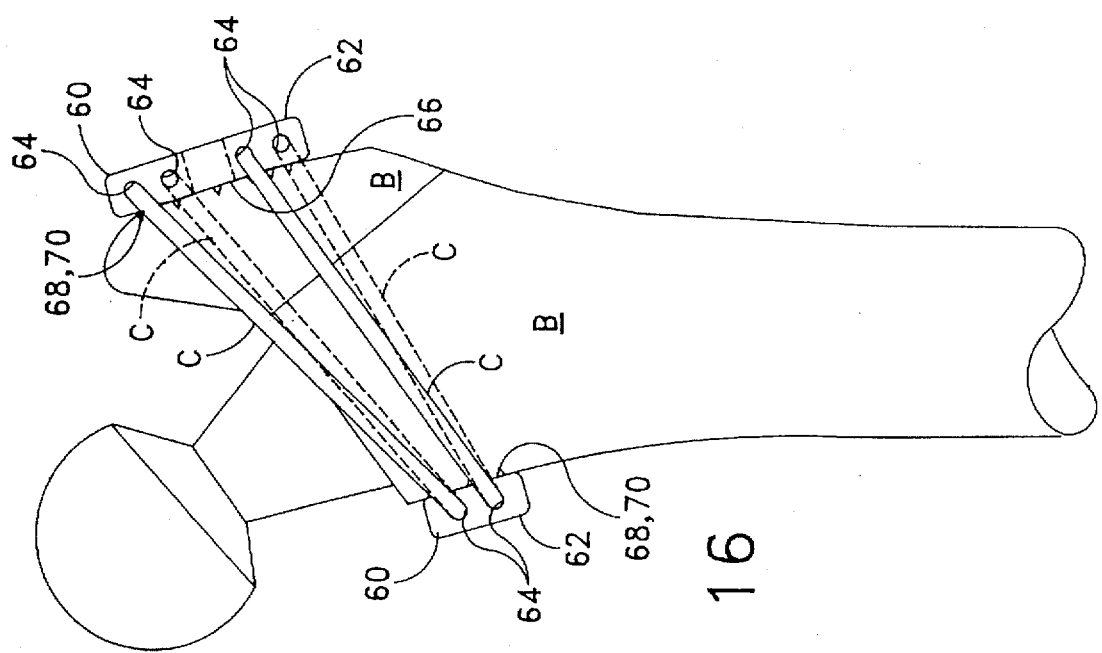
FIG. 16 illustrates diagrammatically typical use of the fastener devices of FIGS. 10, 13 and FIGS. 11, 14.

Referring to FIG. 1, there is shown a bone B having a fracture F therein. A compression plate P and surgical cable C are applied to bone B in the area of fracture F to bind together the segments of bone B, all in accordance with prior art teachings. The plate P is provided with a screw hole recess R (FIGS. 1, 2, 5 and 7) and extending therefrom an elongated screw hole H.

In accordance with the present invention, there is provided an improved fastener device, illustrated in the form of a crimp device 20, for receiving and retaining cable C. Crimp 20 is of a deformable material, preferably metal, and includes a top block portion 22 having first and second bores 24, 26 extending entirely therethrough from side-to-side and parallel to each other, and adapted to receive and retain surgical cable C. When the fastener device is intended to have cable C welded therein, or retained by one or more screws, or the like, the top block portion 22 obviously need not be deformable.

A protrusion 28 (FIGS. 3, 5 and 7) extends from an underside 30 of top block portion 22 centrally of top block portion 22. In a first embodiment, shown in FIGS. 3, 5 and 7, protrusion 28 includes a bulbous portion 32 depending from underside 30 of top block portion 22, and a cylindrical portion 34 depending from the bulbous portion 32 and centrally thereof. As shown in FIG. 5, bulbous portion 32 is configured and adapted for disposition in recess R of plate P, and cylindrical portion 34 is configured and adapted for disposition in screw hole H of plate P.

As may be seen in FIG. 3, bulbous portion 32 and cylindrical portion 34 of protrusion 28 are circular in bottom plan view, and therefore circular in widthwise cross-section and, as noted above, centered with respect to top block portion 22, such that protrusion 28 is permitted to rotate in plate recess R and screw hole H of plate P.

As may be seen in FIG. 5, first and second bores 24, 26 are disposed equal distances d from, and on opposite sides of, a hypothetical extension 36 of cylindrical portion 34 of protrusion 28 through top block portion 22. Bores 24, 26 extend normal to a lengthwise axis 38 of cylindrical portion 34.

In operation, the segments of bone B are placed together in abutting relationship along the line of fracture F. A compression plate P is placed alongside, and in engagement with, bone B, extending over both segments of bone B (FIGS. 1 and 5). At least one fastener device, such as crimp 20, is placed in plate screw hole recess R (FIG. 5). Cable C is extended through one of the bores 24, 26, around bone B (FIG. 7) and through the other of bores 24, 26. The cable is drawn taut and the crimp device is crimped (not shown), using crimping tools of the type known in the art. Again, the fastener may include means for fixing cable C to the fastener other than by crimping, in which case such other fixing means is utilized in place of crimping.

In the course of tightening the cable C, the bores 24, 26, extending parallel to each other, normal to protrusion axis 38, and equidistant from a hypothetical extension 36 of cylindrical portion 34, are turned in plate screw hole recess R and screw hole H to assume the shortest distance between opposed exposed portions of cable C. The crimp device 20 thereby obviates subsequent loosening of cable caused by the crimp device gradually acceding to cable forces urging the crimp to assume the shortest distance between the exposed cable portions.

In FIGS. 1, 4, 5 and 8, there is shown an alternative embodiment of crimp device 40 configured and adapted for use in conjunction with a fixation screw S having a head portion D with a hexagonally shaped wrench hole W therein (FIG. 6). Crimp 40 is similar to crimp 20, differences being (1) protrusion 28 comprises a cylindrical portion 42 configured and adapted for disposition in wrench hole W in screw head D, and (2) a top block portion 44, on underside 46 thereof, is provided with a recess 48 for receiving fixation screw head D. Crimp 40 is rotatable in screw head wrench hole W. Bores 50, 52 are disposed in top block portion 44 relative to a hypothetical extension of cylindrical portion 42 substantially the same as bores 24, 26 relative to the hypothetical extension 36 of cylindrical portion 34 of the above-described first embodiment.

In use of the second embodiment of crimp 40, fixation screw S is deployed as is customary in the art and crimp 40 is inserted into screw head D. Upon tightening of cable C, crimp 40 is rotatably drawn into providing the shortest distance between exposed portions of cable. Again, while referred to and described as a crimp device, it will be apparent that the fastener device 40 need not depend upon crimping, but may serve the intended purpose by utilizing any of the fixing means, other than crimping, described hereinabove.

Both the first and second embodiments of crimp device 20, 40 are retained by the compression plate recess R and hole H, and therefore refrain from migration along the plate P. Crimp devices 20, 40 may be used at any location on plate P where there is a recess R. Separate crimp recesses, or slots, are not required. Further, the second embodiment of crimp 40 is used in combination with a fixation screw.

Referring to FIG. 5, a comparison of the first and second embodiments of crimps 20, 40 reveals that protrusion 28 of first embodiment 20 is substantially of the same configuration as screw head D shown together with second embodiment 40.

Figure 15:
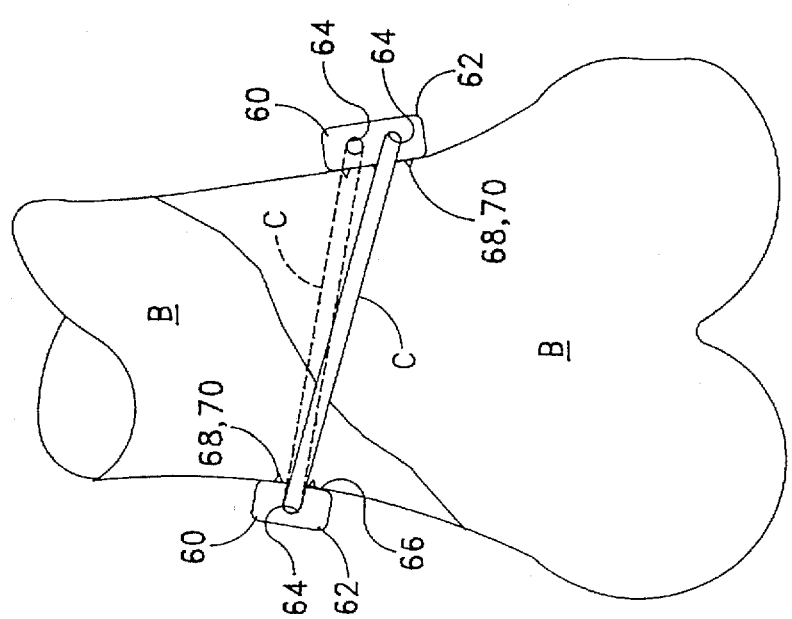
FIG. 15 illustrates diagrammatically typical use of the fastener devices of FIGS. 9, 12 and FIGS. 10, 13.

In FIGS. 9 and 12 there is shown another alternative embodiment of fastener device 60 comprising a block 62 having a bore 64 extending therethrough. An undersurface 66 of block 62 is provided with gripper means 68 thereon for engagement with a bone surface (FIG. 15). The gripper means 68 may comprise bone surface penetration means, such as spike-like elements 70, as shown in FIGS. 9 and 12, or may comprise other gripping means, such as a roughened surface, friction bands, and the like.

In FIGS. 10 and 13, and 11 and 14, there are shown variations of the embodiment shown in FIGS. 9 and 12, having a plurality of bores 64 therethrough and larger undersurfaces 66 with increased areas of gripper means 68. Fasteners 60 are used without compression plates and are applied directly to bone, as shown in FIGS. 15 and 16. Various combinations of fasteners 60 may be used. In FIG. 15, there is illustrated fastener 60 of FIGS. 9 and 12 used in combination with fastener 60 of FIGS. 10 and 13. In this arrangement, wherein the fasteners comprise crimp devices, the crimping is effected on the larger crimp device. Similarly, in FIG. 16 there is illustrated the crimp of FIGS. 10 and 13 used in combination with the crimp of FIGS. 11 and 14. In this arrangement, the crimping is effected on the larger crimp device.

The crimps 60 preferably are of stainless steel, or a cobalt-chromium-molybdenum alloy, or a titanium alloy, and can be bent to conform to a bone contour and, thereafter, be deformed by a crimping tool (not shown) to capture the cable in the crimp device.

In use of crimps 60, tightening of cable C forces gripper means 68 into intimate contact with the surface of bone B. If gripper means 68 constitute bone surface penetration means, such as the spike-like elements 70 shown in FIGS. 9–16, the tightening of cable C serves to urge elements 70 into the bone B, to securely anchor the crimps 60 in the bone.

The crimp devices 20, 40, 60 may be provided with openings 72 (FIG. 14) which facilitate deformation of the crimp device and which, in the larger crimp devices, such as that illustrated in FIG. 14, serve to receive a crimping tool jaw (not shown).

There is thus provided an improved fastener device, which may be provided in the form of a crimp device, adapted for use with known metal compression plates and for use in conjunction with conventional fixation screws. There are further provided fasteners for use in fixation of metaphyseal bone, without need for compression plates. In each embodiment of fastener, the device is held in place during tightening of cable C.

It is to be understood that the present invention is by no means limited to the particular constructions heroin disclosed and/or shown in the drawings, but also comprises any modifications or equivalents within the scope of the claims. For example, while the third embodiment of fastener has been described and illustrated with respect to bone fracture fixation, it will be apparent that such fasteners have utility in the binding together of items generally.

What is claimed is:

1. A surgical fastener device for use in bone fracture fixation, said device comprising:
   a top block portion having bore means extending therethrough, an uppermost top surface, and four side surfaces depending from edges of said top surface; and
   a protrusion integral with and extending from an underside of said top block portion centrally lengthwise and widthwise of said top block portion, said underside being bounded by said four side surfaces; and said top block side surfaces defining the lateral extent of said device.

2. A surgical fastener device in accordance with claim 1 wherein said bore means extend entirely through said top block portion side-to-side, said bore means are adapted to receive surgical cable, and
   said bore means comprise first and second bores disposed equal distances from and on opposite sides outwardly of a hypothetical extension of a cylindrical portion of said protrusion through said top block portion, and extend normal to a lengthwise axis of said cylindrical portion.

3. A surgical fastener device in accordance with claim 1 wherein said protrusion comprises:
   a bulbous portion circular in plan view and curved downwardly and inwardly in side view, and adapted for disposition in a recess in a compression plate, said bulbous portion depending from said top block; and
   a cylindrical portion depending centrally from said bulbous portion and adapted for disposition in a screw hole of the compression plate.

4. A surgical fastener device in accordance with claim 1 wherein said protrusion comprises a cylindrical portion adapted for disposition in a hole in a fixation screw head and is rotatable in the hole, said top block portion having therein a recess for receiving the fixation screw head.

5. A surgical fastener device in accordance with claim 4 wherein said bore means comprise first and second bores which extend entirely through said top block portion and are parallel to each other, and said bores are disposed equal distances from and on opposite sides of and outwardly from a hypothetical extension of said protrusion through said top block portion, and extend normal to a lengthwise axis of said protrusion.

6. A surgical fastener device in accordance with claim 1, wherein said device is a crimp device, in combination with a surgical cable extending through said bore means, said crimp device being deformed upon said cable to hold said cable in said crimp device.

7. A surgical fastener device in accordance with claim 1, wherein said device is a crimp device, in combination with a compression plate having a screw hole recess therein and a screw hole in said recess and extending through said plate, said protrusion being disposed in said screw hole recess and said screw hole.

8. A surgical fastener device in accordance with claim 1, wherein said device is a crimp device, in combination with a compression plate having a screw hole recess therein and a screw hole in said recess and extending through said plate, and a screw having a head portion disposed in said recess and a shaft portion extending through said screw hole, said head portion having a wrench hole therein, and said protrusion extending into said wrench hole and rotatable therein.

9. A surgical fastener device for use in bone fracture fixation, said device comprising a block having a bore extending therethrough, said block having a flat, upper most top surface and four side walls depending from edges of said to surface, and an undersurface with gripper means extending from said undersurface for direct engagement with a bone surface, said gripper means being disposed wholly within hypothetical extensions of said side walls, and comprising bone surface penetrating means.

10. A surgical fastener device in accordance with claim 9 wherein said penetration means comprise spike-like elements.

11. A surgical fastener device in accordance with claim 9 wherein said block is bendable to conform to the bone surface.

12. A surgical fastener device in accordance with claim 9, wherein said fastener device comprises a crimp device, in combination with a surgical cable extending through said bore, said crimp device being deformed upon said cable to hold said cable in said crimp device.

13. A method for binding together first and second bone portions, the method comprising the steps of:

providing a fastener device having a top block portion with bore means extending therethrough, an uppermost top surface, and four side surfaces depending from edges of said top surface, and a protrusion integral with and extending from an underside of said top block portion centrally of said top block portion, said underside being bounded by said four side surfaces, and said top block side surfaces defining the lateral extent of said device;

providing a compression plate having a recess therein and a screw hole in said recess and extending through said plate;

providing a surgical cable;

placing said bone portions in position for binding together; and placing said plate alongside said bone portions and abutting said bone portions, and placing said protrusion in said plate recess and screw hole, and encircling said bone portions with said cable, extending said cable through said bore means, pulling said cable taut, and fixing said cable in said fastener device.

14. A method for binding together first and second bone portions, the method comprising the steps of:

providing a fastener device comprising a block with bore means extending therethrough, said block having a flat, upper most top surface and four side walls depending from edges of said top surface, and an undersurface with gripper means extending from said underside for direct engagement with a surface of one of said bone portions, said gripper means being disposed wholly within hypothetical extensions of said side walls, and comprising bone surface penetrating means;

providing a surgical cable;

placing said bone portions in position for binding together; and placing said device undersurface in engagement with said surface of said one bone portion, and encircling said bone portions with said cable, extending said cable through said bore means, pulling said cable taut, and fixing said cable in said fastener device.

* * * * *